(12) United States Patent
Benammar et al.

(10) Patent No.: US 10,172,982 B2
(45) Date of Patent: Jan. 8, 2019

(54) SYSTEM, APPARATUS, METHOD, AND COMPUTER READABLE MEDIUM FOR MONITORING VOLUME AND RATE OF AIR DRAINED FROM A BODY

(71) Applicant: Qatar University, Doha (QA)

(72) Inventors: Mohieddine Benammar, Doha (QA); Rashid Mazhar, Doha (QA)

(73) Assignee: QATAR UNIVERSITY, Doha (QA)

( * ) Notice: Subject to any disclaimer, the term of this patent is extended or adjusted under 35 U.S.C. 154(b) by 324 days.

(21) Appl. No.: 15/071,053

(22) Filed: Mar. 15, 2016

(65) Prior Publication Data

US 2016/0271304 A1   Sep. 22, 2016

Related U.S. Application Data

(60) Provisional application No. 62/133,622, filed on Mar. 16, 2015.

(51) Int. Cl.
*A61M 1/00* (2006.01)

(52) U.S. Cl.
CPC ........ *A61M 1/0001* (2013.01); *A61M 1/0013* (2013.01); *A61M 1/0021* (2013.01); *A61M 1/008* (2013.01); *A61M 2205/18* (2013.01); *A61M 2205/3334* (2013.01); *A61M 2205/3393* (2013.01); *A61M 2205/3553* (2013.01); *A61M 2205/3584* (2013.01); *A61M 2205/52* (2013.01);
(Continued)

(58) Field of Classification Search
CPC .. A61M 1/0001; A61M 1/008; A61M 1/0013; A61M 1/0021; A61M 2205/18; A61M 2205/3334; A61M 2205/3393; A61M 2205/3553; A61M 2205/3584; A61M 2205/52; A61M 2205/702; A61M 2209/02; A61M 2210/101; A61M 2230/005; A61M 2230/20; A61M 1/0023; A61M 1/006; A61M 1/0058
See application file for complete search history.

(56) References Cited

U.S. PATENT DOCUMENTS 4,592,741 A * 6/1986 Vincent ............... A61M 1/0023
                                                     604/118
4,654,029 A    3/1987 D'Antonio
(Continued)

FOREIGN PATENT DOCUMENTS

EP   1894584   3/2008
EP   2143452   1/2010
(Continued)

OTHER PUBLICATIONS

Cerfolio, R., CTSNet, Clinical Use of a Digital Air Leak System, published Apr. 8, 2008, retrieved Aug. 15, 2014 from http://www.ctsnet.org/portals/thoracic/newtechnology/article-13.
(Continued)

*Primary Examiner* — Adam Marcetich
(74) *Attorney, Agent, or Firm* — Squire Patton Boggs (US) LLP

(57) ABSTRACT

Air drained from a patient's body can be measured after a surgical operation or trauma. The volume of air drained from the body can be determined from the weight of a vessel that has receive effluent drained the body and the volume of air that has escaped from the vessel. The effluent can include any one or a combination of air and liquid.

24 Claims, 6 Drawing Sheets

(52) U.S. Cl.
CPC . *A61M 2210/101* (2013.01); *A61M 2230/005* (2013.01)

(56) References Cited

U.S. PATENT DOCUMENTS

| | | | | |
|---|---|---|---|---|
| 4,772,277 | A * | 9/1988 | Schiller | A61M 1/0013 116/276 |
| 4,773,257 | A * | 9/1988 | Aslesen | G01F 1/86 73/61.44 |
| 5,738,656 | A * | 4/1998 | Wagner | A61M 1/0084 604/119 |
| 5,955,672 | A | 9/1999 | Van Driel et al. | |
| 6,681,615 | B1 | 1/2004 | Svanberg et al. | |
| 7,207,946 | B2 | 4/2007 | Sirokman | |
| 8,157,775 | B2 | 4/2012 | Bobroff et al. | |
| 8,500,673 | B2 | 8/2013 | Zanotti et al. | |
| 2002/0116994 | A1 * | 8/2002 | Heinonen | G01F 1/36 73/196 |
| 2003/0212337 | A1 * | 11/2003 | Sirokman | A61M 1/0013 600/529 |
| 2010/0174270 | A1 * | 7/2010 | Charlez | A61M 1/0013 604/540 |
| 2011/0071415 | A1 * | 3/2011 | Karwoski | A61B 5/08 600/529 |
| 2012/0035560 | A1 * | 2/2012 | Eddy | A61F 13/0203 604/313 |
| 2014/0213992 | A1 | 7/2014 | Ehlert | |
| 2015/0343120 | A1 * | 12/2015 | Yokoi | A61M 1/0013 604/318 |
| 2016/0193393 | A1 * | 7/2016 | Peatfield | A61M 1/0033 604/319 |

FOREIGN PATENT DOCUMENTS

| | | |
|---|---|---|
| EP | 2189171 | 5/2010 |
| JP | H08-187281 | 7/1996 |
| WO | WO98/48866 | 11/1998 |
| WO | WO2004/071279 | 8/2004 |
| WO | WO2011/107972 | 9/2011 |
| WO | WO2011/112291 | 9/2011 |
| WO | WO2013/123338 | 8/2013 |

OTHER PUBLICATIONS

Medela, Thopaz—Thoracic Drainage System, retrieved Aug. 15, 2014 from http://www.medela.com/US/en/healthcare/products/thoracic-drainage/thopaz.html.

* cited by examiner

SYSTEM, APPARATUS, METHOD, AND COMPUTER READABLE MEDIUM FOR MONITORING VOLUME AND RATE OF AIR DRAINED FROM A BODY

CROSS-REFERENCE TO RELATED APPLICATION

This application claims the benefit of U.S. Provisional Application No. 62/133,622, filed Mar. 16, 2015, which is incorporated herein by reference in its entirety and for all purposes.

FIELD

This invention relates generally to medical devices, and more particularly to a system, apparatus, method, and computer readable medium for monitoring the amount of effluent drained from a body cavity.

BACKGROUND

Following an operation or trauma of the chest, tubes are inserted into the thoracic cavity to let the blood and air drain out. Air is usually drained by the principle of underwater seal drainage, whereby it escapes through the outlet tube of a reservoir bottle into the environment either passively or assisted by a suction force. Fluid draining out of the chest is collected inside the reservoir. The reservoir bottle is usually a transparent, graduated vessel placed on the ground level next to the patient's bed.

For clinical management it is important that the surgeon knows the amount and rate of the blood and air draining out of the patient assessed by the Intensive Care Unit (ICU) nurse who has to observe and chart the drainage data at repeated intervals. Current air leak assessment is made in a subjective way by observing the speed and the vigor of bubbling produced from escaping air, under the water seal. There are systems available in the market which purport to monitor air leakage subjectively, examples being "Digivent" by Millicore and "Pleur-evac, Sahara drainage system" by Teleflex Medical.

There are disadvantages with prior art systems. For example, prior art systems do not provide an estimate of air trapped in the "foamy layer" of mixed air/blood drainage from the patient's body cavity. Prior art systems require specifically modified/designed reservoirs with complex devices added to the individual chest drain reservoir bottles, thus making drainage units expensive, bulkier, and cumbersome to use.

Accordingly, there is a need for system, apparatus and method for monitoring the volume and rate of air drained from a body which addresses the disadvantages of prior art systems. There is a need for an objective, real-time, air drainage data system, apparatus, and method capable of sensing and digitally recording air drained from a body.

SUMMARY

Briefly and in general terms, the present invention is directed to measurement of air drained from a patient's body.

In aspects of the invention, an apparatus for measuring air drained from a patient's body comprises a vessel configured to receive air and liquid drained from the body, a weight sensing device configured to weigh the vessel, an airflow sensing device configured to detect airflow out of a vent of the vessel, and a processor device. The processor device is configured to receive signals from the weight sensing device and the airflow sensing device, and is configured or programmed to determine a volume of air drained from the body according to the signals received from the weight sensing device and the airflow sensing device.

In aspects of the invention, a system for measuring air drained from a patient's body comprises the apparatus and one or more display devices communicatively coupled to the processor device of the apparatus. Each display device is configured to receive, store, and display data representing a volume of air drained from the body determined by the processor.

In aspects of the invention, a method for measuring air drained from a patient's body comprises determining a weight of a vessel that has receive effluent drained from the body. The effluent includes any one or a combination of air and liquid. The method further comprises determining a volume of air that has escaped from the vessel, and determining a volume of air that has drained from the body according to the determined weight of the vessel and the determined volume of air that has escaped from the vessel.

In aspects of the invention, a non-transitory computer readable medium has a stored computer program embodying instructions, which when executed by a computer, causes the computer to perform one or more steps for measuring air drained from a patient's body. The computer readable medium comprises instructions for determining a weight of a vessel that has received effluent drained from the body. The effluent includes any one or a combination of air and liquid. The computer readable medium further comprises instructions for determining a volume of air that has escaped from the vessel, and instructions for determining a volume of air that has drained from the body according to the weight of the vessel and the volume of air that has escaped from the vessel.

The features and advantages of the invention will be more readily understood from the following detailed description which should be read in conjunction with the accompanying drawings.

DETAILED DESCRIPTION OF EXEMPLARY EMBODIMENTS

Figure 1:
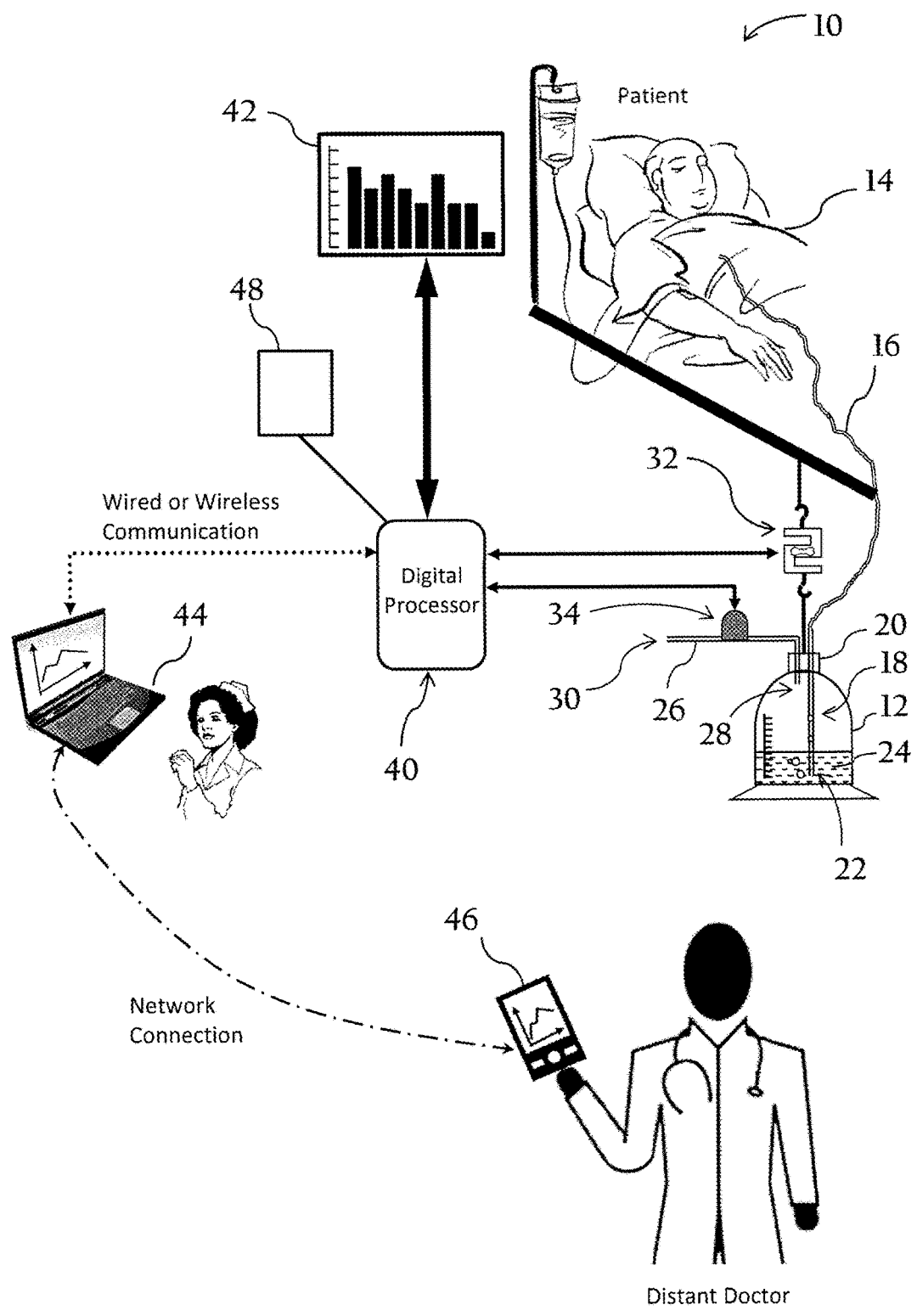
FIG. 1 is a diagram showing an exemplary system for monitoring the volume and rate of air drained from a body.

Referring now in more detail to the exemplary drawings for purposes of illustrating embodiments of the invention, wherein like reference numerals designate corresponding or like elements among the several views, there is shown in FIG. 1 system 10 for monitoring the volume and rate of air drained from a body. The system comprises vessel 12 connected to a patient's body 14 by drainage tube 16. Optionally, a plurality of drainage tubes may connect vessel 12 to body 14. Vessel 12 is incompressible or non-collapsible and is made of rigid or semi-rigid material. For example and without limitation, vessel 12 can be made of glass, thermoplastic, ceramic, or metal. Optionally, vessel 12 is made of a transparent material, such as clear glass or thermoplastic. Vessel 12 can be a disposable under-seal drainage bottle used in hospitals.

Drainage tube 16 receives from body 14 effluents 18, such as blood and/or air, draining out of body 14. Drainage tube 16 conveys effluents 18 to vessel 12, which is located below body 14. Vessel 12 receives effluents 18 on the principle of underwater seal drainage. Vessel 12 includes a fluid- and air-tight cap 20. Drainage tube 16 passes through cap 20. Cap 20 may be removable from the body of vessel 12. Effluent outlet opening 22 of drainage tube 16 is disposed within vessel 12 and submerged below the surface of liquid 24 within vessel 12.

Vessel 12 contains air above the surface of liquid 24. Air that drains from body 14 exits effluent outlet opening 22 of drainage tube 16 and bubbles up to the surface of liquid 24. Blood that drains from body 14 collects within vessel 12. Vent tube 26 passes through cap 20. Vent tube 26 allows air to escape out from vessel 12, either unassisted or assisted with negative pressure or suction. Air inlet opening 28 of vent tube 26 is disposed within vessel 12 and located above the surface of liquid 24. Air outlet opening 30 of vent tube 26 is disposed outside of vessel 12. Cap 20 is configured such that no air can escape from within vessel 12 except through vent tube 26. Liquid 24 prevents air within vessel 12 from entering drainage tube 16.

Effluent 18, such as air and/or blood, which enters vessel 12 through drainage tube 16 causes displacement of an equal volume of air already present in vessel 12. Vessel 12 is coupled to weight sensing device 32 and airflow sensing device 34. Weight sensing device 32 is configured to detect the weight or mass of the contents of vessel 12. Airflow sensing device 34 is configured to detect an amount or volume of air moving through vent tube 26.

Signals from weight sensing device 32 and airflow sensing device 34 are communicated to processor device 40. Processor device 40 can be a digital device. For example, processor device 40 may include a microcontroller, integrated circuits, memory storage components (e.g., hard disc drive, optical drive, flash drive, other non-volatile memory components, and/or volatile memory components, etc.). The signals generated by devices 32, 34 may be digital or analog signals. The signals may be communicated to processor device 40 via cables, via radio frequencies, optically, or any known means of wired communication, wireless communication, and combinations thereof. The signals from weight sensing device 32 are representative of a change in the weight or mass of the contents of vessel 12, or more particularly representative of volume of blood which has drained from body 14 and collected in vessel 12. The signals from airflow sensing device 34 are representative of air moving through vent tube 26, or more particularly representative of the volume of effluent 18 which has drained or leaked from body 14.

Processor device 40 uses the signals it receives to compute the volume and rate of air drained from body 14. Data representing the volume and rate of air drained from body 14 are communicated by processor device 40 to patient-side display device 42. Patient-side display device 42 is configured to store and display the data. Alternatively or additionally, data representing the volume and rate of air drained from body 14 are communicated by processor device 40 to a medical information device 44. Medical information device 44 is configured to store and display the data. Optionally, medical information device 44 is located away from the patient, such as at a nurse's station. Optionally, medical information device 44 is configured to communicate the data to a mobile device 46, which may be carried by a physician. Mobile device 46 can be a personal digital assistant (PDA), computer tablet, laptop, or mobile telephone. Mobile device 46 allows the physician, which may be located at a distant location, to be informed of the state of the patient. Communication between the processor device 40, patient-side display device 42, medical information device 44, and mobile device 46 can be accomplished via cables, via radio frequencies, optically, or any known means of wired communication, wireless communication, and combinations thereof.

Any one or more of processor device 40, patient-side display device 42, medical information device 44, and mobile device 46 may include a digital processor (e.g., CPU), memory storage components (e.g., hard disc drive, optical drive, flash drive, other non-volatile memory components, and/or volatile memory components, etc.), a graphical display (e.g., liquid crystal display, light emitting diode display, etc.), user input components (e.g., keypad, keyboard, touch-sensitive screen, etc.), as well as electronic transmitters and receivers for data communication. Any one or more of devices 40, 42, 44, 46 may include, store, and execute software that enable the device to compute, receive, store, transmit, and/or display data representative of the volume and rate of air drained from body 14. Software may be embedded software and/or application software.

Figure 2:
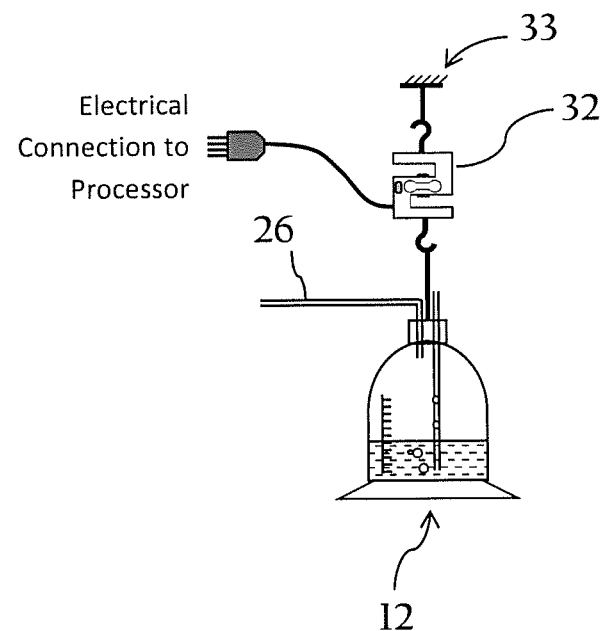
FIG. 2 is a diagram showing an exemplary weight measurement arrangement using an S-type load cell in tension mode, which may optionally be implemented in the system of FIG. 1.

As shown in FIG. 2, weight sensing device 32 may include a load cell operating in tension. For example, weight sensing device 32 may include a load cell configured to measure strain or deflection of an S-shaped body having an upper end suspended and secured to a fixed structure 33, such as a bed frame, and having an opposite end to which vessel 12 is suspended and secured. It will be appreciated that other load cells operating in tension, such as a piezoelectric load sensor, may be implemented.

Figure 3:
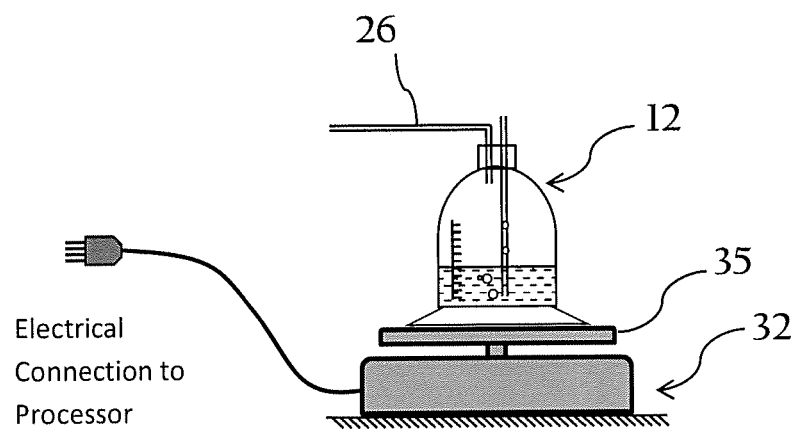
FIG. 3 is a diagram showing an exemplary weight measurement arrangement using an electronic scale in compression mode, which may optionally be implemented in the system of FIG. 1.

As shown in FIG. 3, weight sensing device 32 may include a load cell operating in compression. For example, weight sensing device 32 may include platform 35 on top of which vessel 12 is placed or secured. Platform 35 is coupled to one or more load cells, such as strain gauge load cell and piezoelectric load cell.

In aspects of the invention, weight sensing device 32 is capable of being used with a variety of different vessels and is not necessarily dependent upon the size and shape of the vessel. For example, it is possible for any incompressible or non-collapsible vessel to be suspended from the weight sensing device 32 of FIG. 2. Also, it is possible for any incompressible or non-collapsible vessel to be placed on top of the weight sensing device 32 of FIG. 3. After monitoring of the patient is completed, weight sensing device 32 can be separated from the vessel and, optionally, weight sensing device 32 can be used again to monitor another patient or the same patient using another collection vessel.

Referring again to FIG. 1, airflow sensing device 34 is attached to vent tube 26 and is configured to measure air escaping from vessel 12. The air escaping from vessel 12 is the sum of air, blood, and foamy air/blood mixture leaking from body 14 and entering vessel 12. Airflow sensing device 34 can be a microelectromechanical (MEMS) mass flow sensor. For example, Model D6F-P mass flow sensors available from Omron Electronic Components LLC (Schaumburg, Ill.) and similar sensors may be used.

Figure 4A:
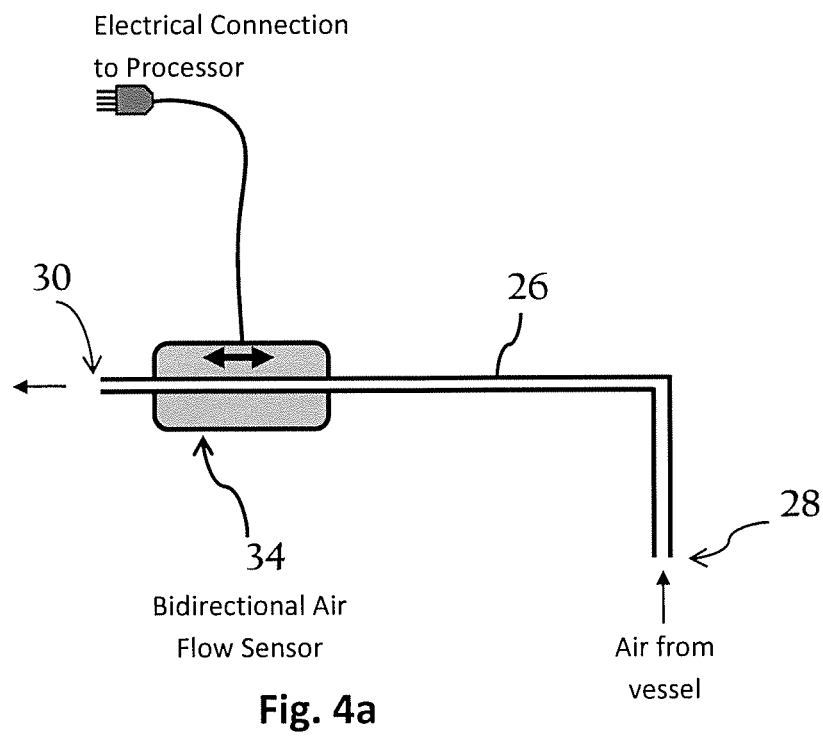
FIG. 4A is a diagram showing an exemplary airflow measurement arrangement using a bidirectional airflow sensor, which may optionally be implemented in the system of FIG. 1.
Figure 4B:
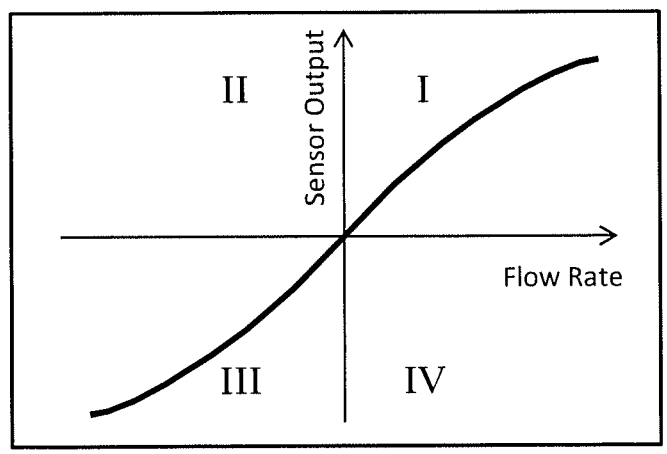
FIG. 4B is a graph showing an exemplary output signal capability of the bidirectional airflow sensor of FIG. 4A.

Airflow sensing device 34 is configured to measure and detect air flowing out of and into vessel 12 via vent tube 26. This allows for compensation for any back airflow that might arise from respiratory movements of the patient or any other reason. Back airflow is defined as air moving through vent tube 26 into vessel 12. For example and without limitation, compensation of back airflow may achieved with airflow sensing device 34 being a bidirectional airflow sensor, as shown in FIG. 4A. The bidirectional airflow sensor is configured to measure and detect air flowing into and out of vessel 12 via vent tube 26. The bidirectional airflow sensor can be a MEMS mass flow sensor including a heater and temperature sensors which detect changes in temperature distribution cause by air flow in two directions. Alternatively, the MEMS mass flow sensor may include capacitive pressure sensors configured to detect airflow in two directions. As shown in FIG. 4B, signal output of bidirectional airflow sensor 34 may indicate positive flow (representing air flowing out of vessel 12) in the first quadrant (I) of the graph at a particular time, and negative flow (representing air flow into vessel 12, also referred to as back airflow) in the third quadrant (III) of the graph at a particular time.

Figure 5A:
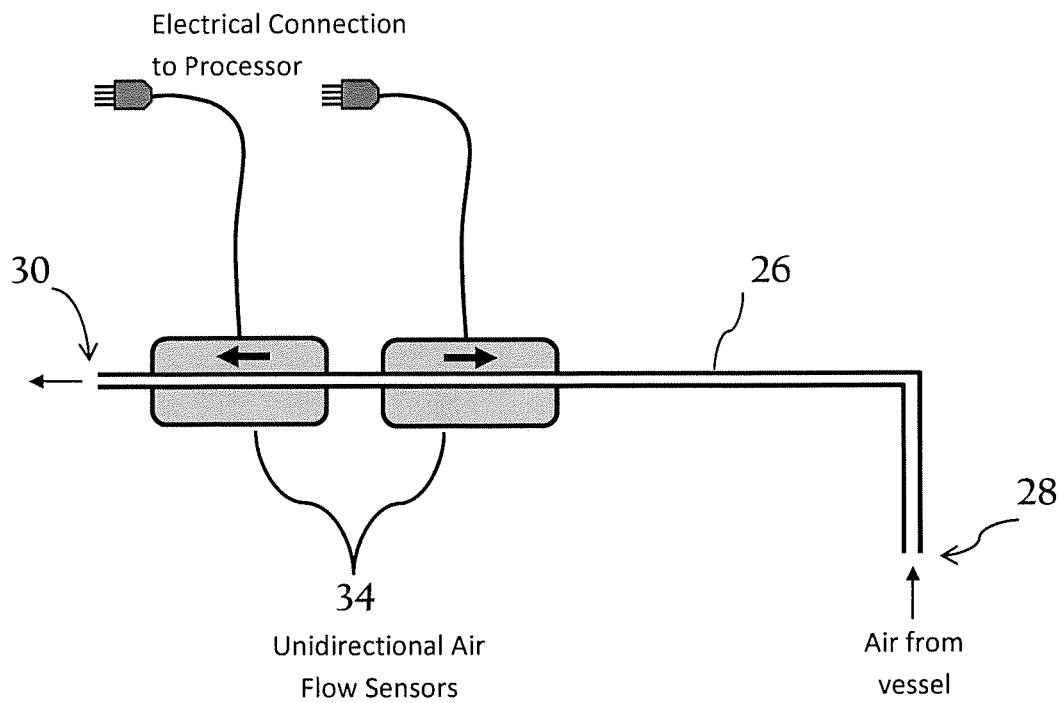
FIG. 5A is a diagram showing an exemplary airflow measurement arrangement using two unidirectional airflow sensors mounted back to back, which may optionally be implemented in the system of FIG. 1.
Figure 5B:
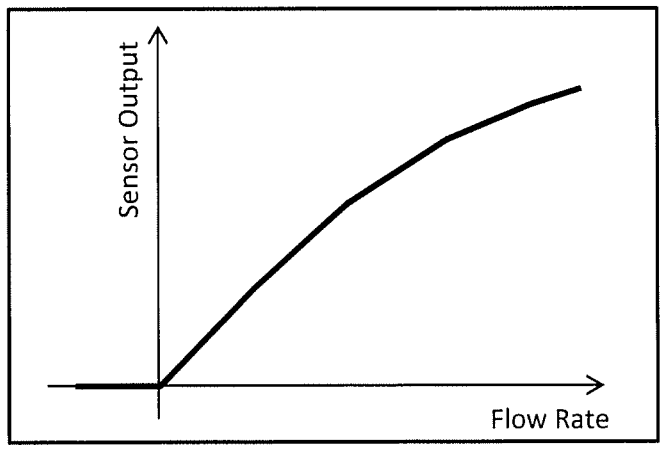
FIG. 5B is a graph showing an exemplary output signal capability of each unidirectional airflow sensor of FIG. 5A.

Compensation for back airflow may achieved with airflow sensing device 34 being two unidirectional airflow sensors connected back-to-back, as shown in FIG. 5A. One of the unidirectional airflow sensors is configured and arranged to measure and detect air flowing out of vessel 12 via vent tube 26. The other one of the unidirectional airflow sensors is configured and arranged to measure and detect air flowing into vessel 12 via vent tube 26. Each unidirectional airflow sensor can be a MEMS mass flow sensor including a heater and a temperature sensor which detects a change in temperature distribution cause by air flow in a single direction. Alternatively, the MEMS mass flow sensor may include capacitive pressure sensors configured to detect airflow in a single direction. As shown in FIG. 5B, signal output of each unidirectional airflow sensor 34 may indicate flow only in the first quadrant (I) of the graph at a particular time. For one of the unidirectional airflow sensors, a positive flow signal represents air flowing out of vessel 12. The other unidirectional airflow sensor is oriented in the opposite direction, so a positive flow signal for that sensor represents air flowing into vessel 12, also referred to as back airflow.

Signals for the bidirectional or unidirectional airflow sensors can be communicated through a direct electrical connection to processor device 40. It will be appreciated that the signals may also be communicated to processor device 40 using any known means of wired communication, wireless communication, or combinations thereof.

As mentioned above, signals from both weight sensing device 32 and airflow sensing device 34 are received as input by processor device 40. Processor device 40 computes the net volume and rate of air leaking from the patient based on the input.

In aspects of the invention, airflow sensing device 34 is capable of being used with a variety of different vessels and is not necessarily dependent upon the size and shape of the vessel. For example, it is possible for airflow sensing device 34 to be coupled to the vent tube or vent orifice or any incompressible or non-collapsible vessel. After monitoring of the patient is completed, airflow sensing device 34 can be separated from the vent or vent tube of the vessel and, optionally, airflow sensing device 34 can be used again to monitor another patient or the same patient using another vessel.

Since the drainage vessel is not compressible or not collapsible, the total volume of liquid and/or blood (Vf) and air leaking (Va) out from body 14 and entering vessel 12 is equal to the total volume of air (Vout) exiting vessel 12. The volume of effluent 18 (such as liquids/blood and foamy blood/air mixture) (Vf+Va) accumulating in vessel 12 displaces an equal volume of air (Vout) that escapes from vent tube 26. The volume of air leaking from the patient's body (Va) causes an equal volume of air to exit the vessel 12, which is true even if the air leaking from the patient is trapped in the blood (e.g., foamy mixture of air and blood) since the trapped air displaces an equal amount of air that exits vessel 12.

Figure 6:
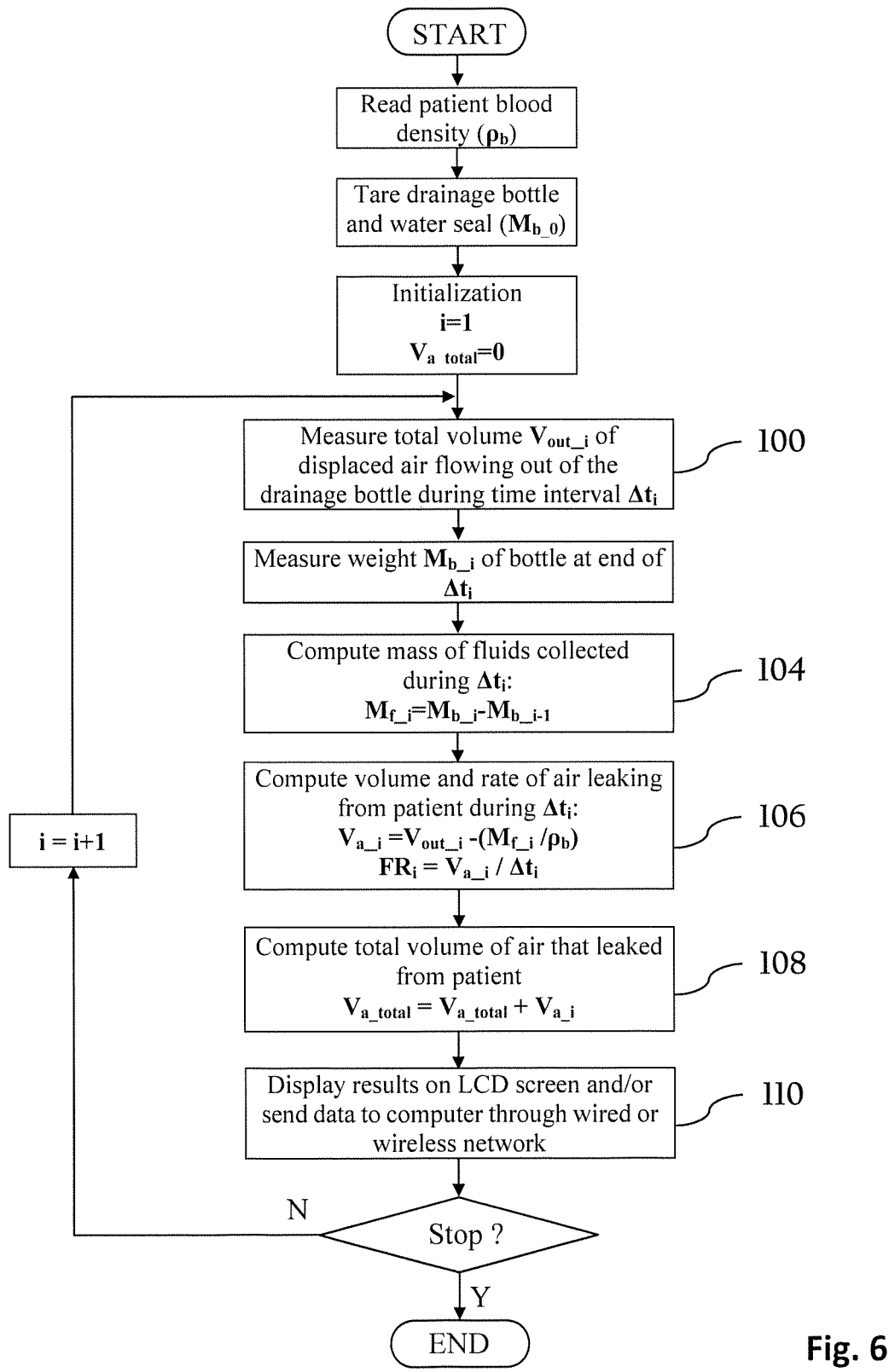
FIG. 6 is a flow chart showing an exemplary method for determining the rate and volume of air drained out of the patient, which may optionally be implemented with the system of FIG. 1 and any one or a combination of the weight measurement arrangements and airflow measurement arrangements of FIGS. 2-5.

Processor device 40 may compute the net air leak from the patient in accordance with method consistent with the flow diagram of FIG. 6. Although the flow diagram of FIG. 6 is described below with reference to elements of system 10 described above, it will be appreciated that the method can be performed using other monitoring systems.

The air leakage from the patient (Va_i) during a time interval Δti can be estimated by processor device 40 as the difference between the corresponding total air exiting the vessel (Vout_i) and estimated liquid/blood volume in the vessel (Vf_i) according to the following equation.

$$Va\_i = Vout\_i - Vf\_i = Vout\_i - (Mf\_i / \rho b)$$

The letter "i" identifies a particular time interval. The calculation can be repeated for a sequence of time intervals, i=1, 2, 3 and so forth.

At block 100 of FIG. 6, Vout_i is determined by processor device 40 using signals from airflow sensing device 34 which is configured to provide signals indicative of movement of air into and out of vessel 12. Compensation for any back airflow is performed. For example, at any given time interval Δti, measurement Vout_i is determined by subtracting measurements of air flowing into vessel 12 (i.e., back airflow) from measurements of air flowing out of vessel 12.

Processor device 40 computes Vf_i from Mf_i and ρb. Mf_i is the mass of liquids collected in the vessel 12 during time interval Δti, and ρb is the blood density. Mf_i is determined at block 104 by processor device 40 using signals from weight sensing device 32. The blood density, ρb, of the patient may be assumed constant and equal to 1.050 g/cm³. The simplification of fixing ρb at 1.050 g/cm³ eliminates the need for repeated estimation of the patient's hematocrit while ensuring an error below 1.5% in plotting the trend of the air leakage and bleeding rate from the patient.

Alternatively, processor device 40 may use the actual value of the patient's blood density, ρb, which may not be precisely equal to 1.050 g/cm³. For example, processor device 40 can be coupled to an optional input device 48 (e.g., keypad, keyboard, touch-sensitive screen, etc.) which allows a nurse, physician, or other person to enter a value for the patient's blood density, ρb.

At block 106 of FIG. 6, processor computes Va_i from Vout_i and from the computed value of Vf_i. Processor device 40 uses the computed value for Va_i to compute the flow rate, FRi, of air drained from the patient during each time interval Δti. Processor may compute FRi according to the following equation.

$$FRi = Va\_i/\Delta ti$$

The value for the time interval, Δti, can be determined or regulated by processor device 40 based on an electronic clock function or component within processor device 40. The time interval implemented by processor device 40 can be 1 second, 2 seconds, 5, seconds, 10 seconds, 30 seconds, or 1 minute. Other time intervals can be implemented by processor device 40.

At block 108 of FIG. 6, processor device 40 may determine the total (accumulated) air drained from the patient by summing all measured Va_i starting from the instant system 10 is connected to the patient. At block 110, processor device 40 may communicate any of Va_i, FRi, and the total air drained from the patient to any one or more of patient-side display device 42, medical information device 44, and mobile device 46. Medical information device 44 may communicate any of Va_i, FRi, and the total air drained from the patient to mobile device 46.

Figure 7:
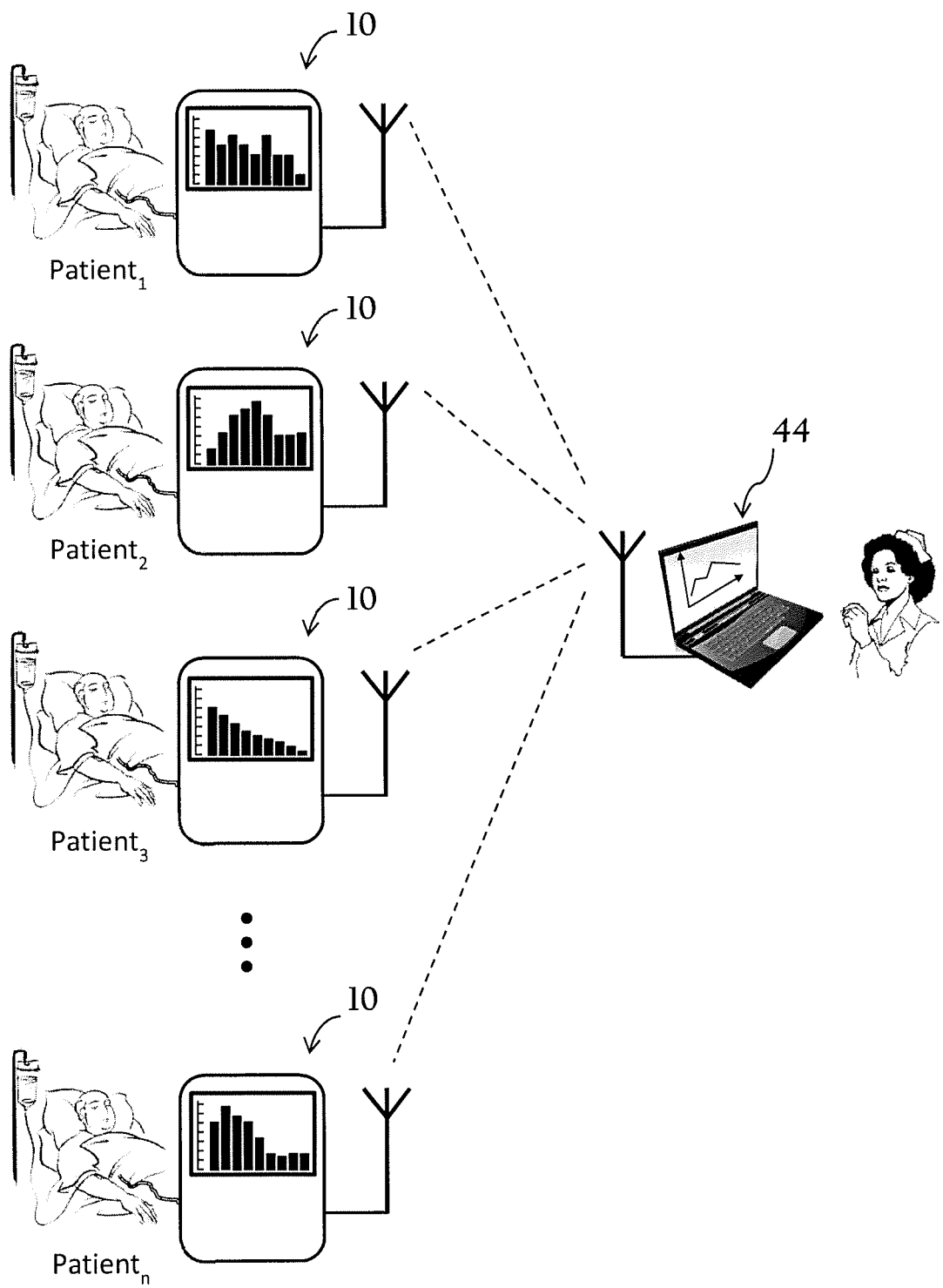
FIG. 7 is a diagram showing an exemplary system for monitoring the volume and rate of air drained from multiple patients being monitored simultaneously and remotely via wireless communication.

As shown in FIG. 7, system 10 can be used for a plurality of patients. The various systems 10 allow for simultaneous monitoring of multiple patients. For example, the processor or patient-side display device in each of systems 10 can transmit data representative of any of Va_i, FRi, and the total air to a single medical information device 44, such as at a nurse's station which may be located at a central location away from the patients. Data from each patient can be identified using an identification code unique to the device transmitting the data. Data can be transmitted via cables, via radio frequencies, optically, or any known means of wired communication, wireless communication, or combinations thereof. For example, ZigBee technology may be used to facilitate wireless communication. ZigBee is a specification, based on an IEEE 802.15.4 standard, for communication protocols used in personal area networks.

System 10 includes an alarm function to alert the medical staff locally and distantly, in the event of unacceptable amounts/rate of air leak, enabling them to exercise accurate and prompt action. The range or threshold for triggering the alarm can be set by medical personnel in dependence upon the patient's clinical condition. The range or threshold for triggering the alarm can be set by numerical entry using an input device (e.g., keypad, keyboard, touch-sensitive screen, etc.) operatively coupled to any one of processor device 40, patient-side display device 42, medical information device 44, and mobile device 46. The alarm can be any one or a combination of sound signal (such as a loud audible tone or pre-recorded message), a visible signal (such as a flashing light or graphic icon on a display screen), and a text message.

From the foregoing description, it will be appreciated that system 10 optionally provides a digital display located at the patient bedside as well as the means to transmit and store air leak data (e.g., Va_i, FRi, and/or the total air drained from the body) locally and distantly via remote means either to a remote personal computer (PC) or personal data assistant (PDA) to allow remote monitoring of the patient. In addition, system 10 may provide for total pattern of air drainage from the present patient as well as historical records of several patients, thus facilitating quality assurance, audit and research in these areas.

From the foregoing description, it will be appreciated that system 10 provides for electronic weighing arrangement 32 of drain reservoir 12 and further provides airflow sensing arrangement 34 at an outlet of reservoir 12. Sensing arrangement 34 may optionally be in the form of a bidirectional sensor or two unidirectional sensors that allows for processor device 40 to compensate for back airflow or negative suction-led flow and provides the net air leaking out of the drainage reservoir. Signals from both these weighing and airflow sensing arrangements are fed into a processor device 40 that computes the net air leak volume and rate. The computed data is then stored and displayed at patient-side display system 42 and/or transmitted, stored, and displayed remotely to dedicated arrangement 44.

In an exemplary aspect, an apparatus is provided for monitoring air draining from a body of a patient. The apparatus comprises vessel 12 for receiving any blood drained with air, weighing arrangement 32 for measuring the weight of the received blood in the vessel, airflow sensing arrangement 34 at an outlet of the vessel for measuring the total airflow out of the vessel, processor device 40 communicatively coupled to the weighing arrangement and the airflow sensing arrangement for calculating rates at which blood and air are leaking from the patient, and an output arrangement for outputting an indication of the air leak volume and rate. Optionally, the output arrangement can be any one of a patient-side display device 42, a medical information device 44, and a mobile device 46.

In an exemplary aspect, a method is provided for monitoring air draining from a body of a patient. The method comprises receiving any blood drained with air in vessel 12, measuring the weight of the received blood in the vessel, measuring at an outlet of the vessel the total airflow out of the vessel, using processor device 40 to calculate the rate at which air leaks from the patient, and outputting an indication of the air leak volume and rate.

The above described apparatus, system, and method allow for a convenient and accurate way of measuring air leak from the total displacement of air from an airtight vessel reservoir 12. Air leakage volume and rate may be calculated using a measurement of the airflow out of the vessel and weight of the vessel. Reservoir 12 could be a single-chamber disposable vessel which only needs airflow sensing device 34 and weight sensing device 32 for the determination of the air leak from the patient. The sterility of the vessel is not compromised by such arrangement. No complicated volume or airflow measurement device or arrangement is required.

The output arrangement can include any suitable device for outputting the results of the air leak calculation, such as Va_i, FRi, and/or the total air. The output arrangement can be a display screen which can be part of processor device 40, patient-side display device 42, medical information device 44, and/or mobile device 46. The output arrangement can be a printer so that output information regarding Va_i, FRi, and/or the total air can be printed. The output information could also be transmitted remotely to remote monitoring devices. The remote monitoring devices can be connected by a wired arrangement or a wireless arrangement to the apparatus. One such configuration uses the Internet which provides one or both of a wired and wireless capability. The remote monitoring devices can be mobile Internet-capable devices such as Internet-enabled mobile telephones and computer tablets.

The output arrangement may include an alarm function that generates an alarm when the volume and/or rate of the air leak is outside a range of values or exceeds a threshold value. This range or threshold can be set by a medical adviser such as a surgeon in dependence upon the patient's clinical condition. The alarm may include at least one or more portable alarm devices and a transmission arrangement for transmitting an alarm signal to each remote portable alarm device. The transmission arrangement can be configured to transmit air-leak information (e.g., Va_i, FRi, and/or the total air drained from the body) over time, and each portable alarm is adapted to receive the transmitted air-leak information in addition to the alarm signal to enable each portable alarm device to display the information. For example, the alarm may be part of display device 42, medical information device 44, and/or mobile device 46. The transmission arrangement (e.g., a transmitter device configured for wired or wireless communication) can be part of processor device 40.

Although only one vessel 12 is illustrated in FIG. 1, it will be appreciated that system 10 may include a plurality of vessels. Each vessel would be coupled to its own set of weight sensing device 32 and airflow sensing device 34. A single processor device 40 can receive signals from all the weight sensing devices and airflow sensing devices corresponding to the various vessels, and the single processor device can measure and compute the combined air-leak (e.g., Va_i, FRi, and/or the total air drained from the body) measured from all the vessels.

In an exemplary aspect, a system is provided for monitoring the volume of air draining from a body of a patient. The system comprises an air-leak measuring arrangement for measuring the volume of air drained from the body, a transmission arrangement for transmitting air-leak information (e.g., Va_i, FRi, and/or the total air drained from the body) and for transmitting an alarm signal when the measured air-leak is outside a range, and at least one remote portable monitoring device for receiving the air-leak data information and the alarm signal. Each remote portable monitoring device comprises an alarm device for generating an alarm when the alarm signal is received. Each remote portable monitoring device further comprises a display for displaying the received air-leak data over time information for the patient.

In an exemplary aspect, a method is provided for monitoring the volume of air drained from a body of a patient. The method comprises measuring the volume of air drained from the body, transmitting air-leak data information (e.g., Va_i, FRi, and/or the total air drained from the body) and an alarm signal when the measured air-leak information is outside a range of values, and receiving the air-leak data information and the alarm signal at one or more remove portable monitoring devices. The remote portable monitoring device can generate an alarm when the alarm signal is received and displays the received air-leak data information to the patient.

A medical adviser can set a range of values outside of which the alarm should be raised. A medical adviser can set a threshold value beyond which the alarm should be raised. Setting the alarm condition (e.g., range of values or a threshold value) allows for automation and simplification of the notification process for the surgical team. If the lead surgeon wishes to be notified to consider re-operation if air-leak (e.g., Va_i, FRi, and/or the total air drained from the body) reaches a threshold, he can set the threshold accordingly and ensure that the whole surgical team is notified if an alarm is raised. Each member of the surgical team may carry a portable monitoring device, such as mobile device 46, so that each member receives the notification. Mobile device 46 can display not just the fact that there is an alarm for a patient, but also the received air-leak data (e.g., Va_i, FRi, and/or the total air drained from the body) which can be displayed graphically to show air leak per unit of time. This provides the necessary data in the same way the surgeons are intuitively trained to make sense of the information, allowing the medical team to decide upon a course of action in the shortest possible time.

Optionally, the transmission arrangement, which can be part of processor device 40 and/or medical information device 44, is configured to transmit to mobile device 46 patient information (such as age of the patient, medication being provided to the patient, medical condition, etc.) in addition to name or other identifying information. This can further remind the surgical team about patients so that they make the appropriate decisions.

The transmission arrangement, which can be part of processor device 40 and/or medical information device 44, can be configured to communicate with mobile device 46 over the Internet, a mobile telecommunications network, a private network, or any combination thereof.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. An apparatus for measuring air drained from a patient's body, the apparatus comprising:
   a vessel configured to receive air and liquid drained from the body;
   a weight sensing device configured to weigh the vessel;
   an airflow sensing device configured to detect airflow out of a vent of the vessel; and
   a processor device configured to receive signals from the weight sensing device and the airflow sensing device, and configured or programmed to determine a volume of air drained from the body accounting for both the signals received from the weight sensing device and the airflow sensing device,
   wherein the volume of air drained from the body is independent of a volume of liquid drained from the body.

2. The apparatus of claim 1, further comprising a drainage tube, the drainage tube including an effluent outlet opening disposed within the vessel, the drainage tube configured to convey air and liquid drained from the body to the vessel.

3. The apparatus of claim 1, wherein the airflow sensing device is configured to detect airflow out of the vent and airflow into the vent, and the processor device is configured to determine the volume of air drained from the body according to signals from the airflow sensing device representing airflow out of the vent and airflow into the vent.

4. The apparatus of claim 1, wherein the processor device is configured to determine the volume of air, Va, drained from the body according to the equation $Va = Vout \, (Mf/\rho b)$, wherein Vout is based on a volume of air that has escaped from the vessel, Mf is based on the weight of the vessel, and ρb is blood density.

5. The apparatus of claim 1, wherein the processor device is configured or programmed to determine a rate of air drained from the body according to the signals received from the weight sensing device and the airflow sensing device.

6. The apparatus of claim 1, wherein the processor device is configured or programmed to transmit data to another device, representing the volume of air drained from the body.

7. The apparatus of claim 6, wherein the processor device is configured or programmed to transmit an alarm signal to the other device when the data representing the volume of air drained from the body satisfies an alarm condition within the processor.

8. A system for measuring air drained from a patient's body, the system comprising:
the apparatus of claim 1;
one or more display devices communicatively coupled to the processor device of the apparatus, each display device configured to receive, store, and display data representing a volume of air drained from the body determined by the processor.

9. The system of claim 8, wherein each display device is configured to generate an alarm when the data satisfies an alarm condition within the display device or within the processor device.

10. The system of claim 8, wherein the one or more display devices include any one or more of a patient-side display device, a medical information device, and a mobile device.

11. A method for measuring air drained from a patient's body, the method comprising:
determining a weight of a vessel that has received effluent drained from the body, the effluent including any one or a combination of air and liquid;
determining a volume of air that has escaped from the vessel; and
determining a volume of air that has drained from the body accounting for both the determined weight of the vessel and the determined volume of air that has escaped from the vessel,
wherein the volume of air drained from the body is independent of a volume of liquid drained from the body.

12. The method of claim 11, wherein determining the weight of the vessel includes receiving a signal from a weight sensing device representative of the weight of the vessel, and determining the volume of air that has escaped from the vessel includes receiving a signal from an airflow sensing device representative of the volume of air that has escaped from the vessel.

13. The method of claim 11, wherein determining the volume of air that has escaped from the vessel includes receiving a first signal from the airflow sensing device representative of the volume of air that has escaped from a vent of vessel, and a second signal from the airflow sensing device representative of a volume of air that has entered the vent.

14. The method of claim 11, wherein determining the volume of air, Va, that has escaped from the vessel is performed according to the equation $Va = Vout\ (Mf/\rho b)$, wherein Vout is based on the determined volume of air that has escaped from the vessel, Mf is based on the determined weight of the vessel, and ρb is blood density.

15. The method of claim 11, further comprising determining a rate of air drained from the body according to the determined weight of the vessel and the determined volume of air that has escaped from the vessel.

16. The method of claim 11, further comprising transmitting data from a processor device to one or more display devices, representing the determined volume of air that has drained from the body, wherein each display device is configured to receive, store, and display the data representing the determined volume of air that has drained from the body.

17. The method of claim 16, further comprising transmitting an alarm signal to the one or more display devices when the data representing the determined volume of air that has drained from the body satisfies an alarm condition within the processor.

18. The method of claim 16, further comprising generating an alarm from the one or more display devices when the data representing the determined volume of air that has drained from the body satisfies an alarm condition within the respective display device.

19. A non-transitory computer readable medium having a stored computer program embodying instructions, which when executed by a computer, causes the computer to perform one or more steps for measuring air drained from a patient's body, the computer readable medium comprising:
instructions for determining a weight of a vessel that has received effluent drained from the body, the effluent including any one or a combination of air and liquid;
instructions for determining a volume of air that has escaped from the vessel; and
instructions for determining a volume of air that has drained from the body accounting for both the weight of the vessel and the volume of air that has escaped from the vessel,
wherein the volume of air drained from the body is independent of a volume of liquid drained from the body.

20. The non-transitory computer readable medium of claim 19, wherein the instructions for determining the volume of air, Va, that has drained from the body is in accordance with the equation $Va = Vout - (Mf/\rho b)$, wherein Vout is based on the volume of air that has escaped from the vessel, Mf is based on the weight of the vessel, and ρb is blood density.

21. The non-transitory computer readable medium of claim 19, further comprising instructions for determining a rate of air drained from the body according to the weight of the vessel and the volume of air that has escaped from the vessel.

22. The non-transitory computer readable medium of claim 19, wherein the instructions for determining a volume of air that has escaped from the vessel includes instructions to compensate for back airflow by subtracting a volume of air that has entered a vent of the vessel from a volume of air that has escaped from the vent of the vessel.

23. The non-transitory computer readable medium of claim 19, further comprising instructions to transmit data from a processor device to one or more display devices, representing the volume of air that has drained from the body.

24. The non-transitory computer readable medium of any of claim 23, further comprising instructions to transmit an alarm signal to the one or more display devices when the data representing the determined volume of air that has drained from the body satisfies an alarm condition within the processor.

\* \* \* \* \*